(12) United States Patent
Notté et al.

(10) Patent No.: US 8,884,053 B2
(45) Date of Patent: Nov. 11, 2014

(54) METHOD FOR THE MANUFACTURE OF AMINOALKYLENE PHOSPHONIC ACID

(75) Inventors: Patrick Notté, Wavre (BE); Albert Devaux, Mont-Saint-Guibert (BE)

(73) Assignee: Straitmark Holding AG, Zug (CH)

( * ) Notice: Subject to any disclaimer, the term of this patent is extended or adjusted under 35 U.S.C. 154(b) by 723 days.

(21) Appl. No.: 12/989,306

(22) PCT Filed: Apr. 25, 2009

(86) PCT No.: PCT/EP2009/055000
§ 371 (c)(1),
(2), (4) Date: Dec. 8, 2010

(87) PCT Pub. No.: WO2009/130322
PCT Pub. Date: Oct. 29, 2009

(65) Prior Publication Data
US 2011/0118502 A1    May 19, 2011

(30) Foreign Application Priority Data

Apr. 25, 2008 (EP) ..................................... 08155198
Nov. 21, 2008 (EP) ..................................... 08169648

(51) Int. Cl.
*C07F 9/44* (2006.01)
*C07F 9/38* (2006.01)

(52) U.S. Cl.
CPC .................................. *C07F 9/3817* (2013.01)
USPC ........................................................ 562/11

(58) Field of Classification Search
USPC ........................................................ 562/11
See application file for complete search history.

(56) References Cited

U.S. PATENT DOCUMENTS

| | | | |
|---|---|---|---|
| 3,288,846 A | 11/1966 | Irani et al. | |
| 6,238,637 B1 | 5/2001 | Heise et al. | |
| 6,440,380 B1 | 8/2002 | Heise et al. | |
| 6,476,256 B1 | 11/2002 | Heise et al. | |
| 2011/0008231 A1 | 1/2011 | Schipper | |

FOREIGN PATENT DOCUMENTS

| | | |
|---|---|---|
| CA | 2070949 | 12/1993 |
| DE | 206363 | 1/1984 |
| DE | 222597 | 5/1985 |
| DE | 292214 | 7/1991 |
| EP | 1008552 | 6/2000 |
| EP | 1681294 | 7/2006 |
| EP | 1886976 | 2/2008 |
| EP | 2112156 | 10/2009 |
| GB | 1142294 | 2/1969 |
| GB | 1230121 | 4/1971 |
| HU | 36825 | 10/1981 |
| HU | 199488 | 2/1990 |
| JP | 57075990 | 5/1982 |
| WO | 9640698 | 12/1996 |
| WO | 9943612 | 9/1999 |
| WO | 2009130322 | 10/2009 |

OTHER PUBLICATIONS

"The Direct Synthesis of a-Aminomethylphosphonic Acids, Mannich-Type Reactions with Orthophosphorus Acid," Moedritzer and Irani, J. Org. Chem., vol. 31 pp. 1603-1607 (1966).

*Primary Examiner* — Sikarl Witherspoon
(74) *Attorney, Agent, or Firm* — Husch Blackwell LLP

(57) ABSTRACT

A method for the manufacture of amino alkylene phosphonic acids is disclosed. Pure $P_4O_6$ is hydrolyzed in the presence of a homogeneous Broensted acid catalyst whereby the pH of the reaction medium is maintained below 5 and the free water content of said reaction medium is, after the $P_4O_6$ hydrolysis has been completed, from 0 to 40%. The required amine component can be added before, during, or in one preferred execution, after the $P_4O_6$ hydrolysis has been completed. Formaldehyde is then added and the reaction mixture containing the $P_4O_6$ hydrolysate, the amine and the formaldehyde is reacted in presence of a Broensted acid catalyst selected from homogeneous and heterogeneous species. The amino alkylene phosphonic acid reaction product can then be recovered in a manner known per sé.

16 Claims, No Drawings

METHOD FOR THE MANUFACTURE OF AMINOALKYLENE PHOSPHONIC ACID

CROSS REFERENCE TO RELATED APPLICATIONS

This application is a U.S. National Phase Application of International Application PCT Application No. PCT/EP2009/055000, filed on Apr. 25, 2009, which claims the benefit of priority from European Patent Application No. 08155198.8, filed on Apr. 25, 2008, and European Patent Application No. 08169648.6 filed on Nov. 21, 2008. The disclosures of International Application PCT Application No. PCT/EP2009/055000, European Application 08155198.8, and European Application 08169648.6 are incorporated herein by reference.

This invention relates to a beneficial method for the manufacture of aminoalkylene phosphonic acid starting from tetra phosphorus hexa oxide. In more detail, $P_4O_6$ is hydrolysed in the presence of a homogeneous Broensted acid and an amine which can be added to the aqueous reaction medium either before the addition of the $P_4O_6$, simultaneously with the $P_4O_6$, or after the addition/hydrolysis of the $P_4O_6$ has been completed, to thus yield, dependent upon the reactant ratios, a combination of phosphorous acid intermediate, a Broensted acid and, in the event the $P_4O_6$ hydrolysis is carried out in the presence of an amine, a conjugated amine salt, wherein the free water level in the reaction medium, after the hydrolysis of the $P_4O_6$ has been completed, is in the range of from 0 to 40%, based on the reaction medium before formaldehyde addition (100%), and wherein the addition of the Broensted acid is effected so that, during the $P_4O_6$ hydrolysis, the pH of the reaction medium is maintained below 5, followed by reacting the medium with formaldehyde, in the presence of a homogeneous Broensted acid having a pKa of equal to or below 3.1 or a selected heterogeneous Broensted acid catalyst, thereby respecting specifically defined reactant ratios, to thus yield an aminoalkylene phosphonic acid. The phosphonic acid so formed can be recovered.

Aminoalkylene phosphonic acid compounds are generally old in the art and have found widespread commercial acceptance for a variety of applications including water-treatment, scale-inhibition, detergent additives, sequestrants, marine-oil drilling adjuvants and as pharmaceutical components. It is well known that such industrial applications preferably require amino alkylene phosphonic acids wherein a majority of the N—H functions of the ammonia/amine raw material have been converted into the corresponding alkylene phosphonic acid. The art is thus, as one can expect, crowded and is possessed of methods for the manufacture of such compounds. The state-of-the-art manufacture of amino alkylene phosphonic acids is premised on converting phosphorous acid resulting from the hydrolysis of phosphorus trichloride or on converting phosphorous acid via the addition of hydrochloric acid which hydrochloric acid can be, in part or in total, added in the form of an amine hydrochloride.

The manufacture of amino alkylene phosphonic acids is described in GB 1.142.294. This art is premised on the exclusive use of phosphorus trihalides, usually phosphorus trichloride, as the source of the phosphorous acid reactant. The reaction actually requires the presence of substantial quantities of water, frequently up to 7 moles per mole of phosphorus trihalide. The water serves for the hydrolysis of the phosphorus trichloride to thus yield phosphorous and hydrochloric acids. Formaldehyde losses occur during the reaction which is carried out at mild temperatures in the range of from 30-60° C. followed by a short heating step at 100-120° C. GB 1.230.121 describes an improvement of the technology of GB 1 142 294 in that the alkylene polyaminomethylene phosphonic acid may be made in a one-stage process by employing phosphorus trihalide instead of phosphorous acid to thus secure economic savings. The synthesis of aminomethylene phosphonic acids is described by Moedritzer and Irani, J. Org. Chem., Vol 31, pages 1603-1607 (1966). Mannich-type reactions, and other academic reaction mechanisms, are actually disclosed. Optimum Mannich conditions require low-pH values such as resulting from the use of 2-3 moles of concentrated hydrochloric acid/mole of amine hydrochloride. The formaldehyde component is added drop wise, at reflux temperature, to the reactant solution mixture of aminehydrochloride, phosphorous acid and concentrated hydrochloric acid. U.S. Pat. No. 3,288,846 also describes a process for preparing aminoalkylene phosphonic acids by forming an aqueous mixture, having a pH below 4, containing an amine, an organic carbonyl compound e.g. an aldehyde or a ketone, and heating the mixture to a temperature above 70° C. whereby the amino alkylene phosphonic acid is formed. The reaction is conducted in the presence of halide ions to thus inhibit the oxidation of orthophosphorous acid to orthophosphoric acid. WO 96/40698 concerns the manufacture of N-phosphonomethyliminodiacetic acid by simultaneously infusing into a reaction mixture water, iminodiacetic acid, formaldehyde, a source of phosphorous acid and a strong acid. The source of phosphorous acid and strong acid are represented by phosphorus trichloride.

The use of phosphorus trichloride for preparing aminopolyalkylene phosphonic acids is, in addition, illustrated and emphasized by multiple authors such as Long et al. and Tang et al. in Huaxue Yu H Shijie, 1993 (1), 27-9 and 1993 34(3), 111-14 respectively. Comparable technology is also known from Hungarian patent application 36825 and Hungarian patent 199488. EP 125766 similarly describes the synthesis of such compounds in the presence of hydrochloric acid; along the same lines, JP 57075990 recommends preparing such compounds starting from phosphorous acid by reacting it with an amine in the presence of concentrated hydrochloric acid.

JP patent application 57075990 describes a method for the manufacture of diaminoalkane tetra(phosphonomethyl) by reacting formaldehyde with diaminoalkane and phosphorous acid in the presence of a major level of concentrated hydrochloric acid.

P—O compounds and the hydrolysis thereof are extensively described in the literature. Canadian patent application 2.070.949 divulges a method for the manufacture of phosphorous acid, or the corresponding $P_2O_3$ oxide, by introducing gaseous phosphorus and steam water into a gas plasma reaction zone at a temperature in the range of 1500° K to 2500° K to thus effect conversion to $P_2O_3$ followed by rapidly quenching the phosphorus oxides at a temperature above 1500° K with water to a temperature below 1100° K to thus yield $H_3PO_3$ of good purity. In another approach, phosphorus (I) and (III) oxides can be prepared by catalytic reduction of phosphorus(V) oxides as described in U.S. Pat. No. 6,440,380. The oxides can be hydrolyzed to thus yield phosphorous acid. EP-A-1.008.552 discloses a process for the preparation of phosphorous acid by oxidizing elemental phosphorus in the presence of an alcohol to yield P(III) and P(V) esters followed by selective hydrolysis of the phosphite ester into phosphorous acid. WO 99/43612 describes a catalytic process for the preparation of P(III) oxyacids in high selectivity. The catalytic oxidation of elemental phosphorus to phosphorous oxidation levels is also known from U.S. Pat. Nos. 6,476,256 and 6,238,637.

U. Schwelte, Phosphorus, Sulphur and Silicon and the Related Elements 51/52 (1990) 153-156 discloses the preparation of inorganic and organic phosphorus compounds by reaction of $P_4O_6$ with nucleophilic and electrophilic compounds. DD 222 597 discloses a method for preparing hydroxy phosphonic acids by reacting $P_4O_6$, $H_3PO_3$ and water in a ratio $P_4O_6$: $H_3PO_3$ between 1:0 and 1:20 with a carbonyl compound $R^1$—CO—$R^2$ with the molar ratio phosphorus (III) compound: carbonyl compound 2:1 to 1:2. EP-A 1 886 976 relates to a process for making an amino acid alkyl formaldehyde in the presence of a heterogeneous, with respect to the reaction medium, Bronsted acid catalyst, followed by recovering the amino acid alkyl phosphonic acid formed. EP-A 1 681 294 discloses a method for the manufacture of amino polyalkylene phosphonic acids, under substantial absence of hydrohalogenic acid, based on reacting narrowly defined ratios of phosphorous acid, an amine, a formaldehyde in presence of specific ranges of an acid catalyst having a pKa equal or inferior to 3.1.

DD 206 363 discloses a process for converting $P_4O_6$ with water into phosphorous acid in the presence of a charcoal catalyst. The charcoal can serve, inter alia, for separating impurities, particularly non-reacted elemental phosphorus. DD 292 214 also pertains to a process for preparing phosphorous acid. The process, in essence, embodies the preparation of phosphorous acid by reacting elementary phosphorus, an oxidant gas and water followed by submitting the reaction mixture to two hydrolysing steps namely for a starter at molar proportions of $P_4:H_2O$ of 1:10-50 at a temperature of preferably 1600-2000° K followed by completing the hydrolysis reaction at a temperature of 283-343° K in the presence of a minimal amount of added water.

However, quite in general, $P_4O_6$ is not available commercially and has not found commercial application. The actual technology used for the manufacture of aminoalkylene phosphonic acids is based on the $PCl_3$ hydrolysis with its well known deficiencies ranging from the presence of hydrochloric acid, losses of $PCl_3$ due to volatility and entrainement by HCl. In addition, the control of the reaction temperature is critical to limit $PCl_3$ losses (bp. 76° C.) and avoid LOOPS formation. While the $PCl_3$ hydrolysis is used commercially, the $P_4O_6$ hydrolysis in accordance with the invention herein is not subject to the multiple shortcomings attached to the $PCl_3$ hydrolysis.

(*). "LOOPS" stands for lower oxides of phosphorus which are compositionally close to elemental phosphorus but will contain some oxygen. A polymeric composition approaching $(P_4OH)_n$ has been sometimes suggested.

The art in substance contemplates synthesizing aminoalkylene phosphonates in multi step arrangements which, for a cumulative series of reasons, were found to be deficient and economically non-viable. The art manufacturing of the like compounds requires, starting from $P_4$, an $H_3PO_3$ isolation with its inherent deficiencies, including marginal selectivity and yield, a significantly shortened and more efficient processing sequence. As an example of the $P_2O_3$ reactivity, it is slowly oxidized to phosphorus pentoxide by air at room temperature and spontaneously ignites on heating to 70° C. When dissolved in cold water with vigorous agitation, a dilute solution of $H_3PO_3$ is formed. In hot water, the $P_2O_3$ reaction becomes violent forming phosphine, phosphoric acid and red phosphorus (Ullmann's Encyclopedia of Industrial Chemistry, 2002, Wiley-VCH Verlag GmbH).

The inventive technology aims at providing technologically new, economically acceptable routes to synthesize the aminoalkylene phosphonic acid compounds in a superior manner consonant with standing desires.

It is a major object of this invention to manufacture aminoalkylene phosphonic acids with high selectivity and yields. It is another aim of this invention to provide a one step manufacturing arrangement capable of delivering superior compound grades. Yet another object of this invention seeks to synthesize the phosphonic acid compounds in a shortened and energy efficient manner.

The above and other benefits can now be achieved by the technology of this invention, basically a one step arrangement whereby a pure $P_4O_6$ compound is hydrolyzed in the presence of a homogeneous Broensted acid and the phosphorous acid formed will subsequently react with an amine and formaldehyde in the presence of a homogeneous and/or heterogeneous Broensted acid to thus yield the aminoalkylene phosphonic acid.

The term "percent" or "%" as used throughout this application stands, unless defined differently, for "percent by weight" or "% by weight". The terms "phosphonic acid" and "phosphonate" are also used interchangeably depending, of course, upon medium prevailing alkalinity/acidity conditions. The term "ppm" stands for "parts per million". The terms "$P_2O_3$" and "$P_4O_6$" can be used interchangeably. Unless defined differently, pH values are measured at 25° C. on the reaction medium as such.

The invention, basically a single reactive arrangement, amounts to a novel arrangement for the manufacture of aminoalkylene phosphonic acid compounds starting from $P_4O_6$, by hydrolyzing the tetraphosphorus hexa oxide, in the presence of a homogeneous Broensted acid, in an aqueous reaction medium, and by reacting the hydrolysate with an amine and formaldehyde in the presence of a homogeneous and/or heterogeneous Broensted acid catalyst. In more detail, the invention herein comprises a method for the manufacture of aminoalkylene phosphonic acid having the general formula:

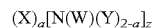

$$(X)_a[N(W)(Y)_{2-a}]_z$$

wherein X is selected from $C_1$-$C_{200000}$, preferably $C_1$-$C_{50000}$, most preferably $C_1$-$C_{2000}$, linear, branched, cyclic or aromatic hydrocarbon radicals, optionally substituted by one or more $C_1$-$C_{12}$ linear, branched, cyclic or aromatic groups (which radicals and/or which groups can be) optionally substituted by OH, COOH, COOG, F, Br, Cl, I, OG, $SO_3H$, $SO_3G$ and SG moieties; $ZPO_3M_2$; [V—N(K)]$_n$—K; [V—N(Y)]$_n$—V or [V—O]$_x$—V; wherein V is selected from: a $C_{2-50}$ linear, branched, cyclic or aromatic hydrocarbon radical, optionally substituted by one or more $C_{1-12}$ linear, branched, cyclic or aromatic groups (which radicals and/or groups are) optionally substituted by OH, COOH, COOR', F/Br/Cl/I, OR', $SO_3H$, $SO_3R'$ or SR' moieties, wherein R' is a $C_{1-12}$ linear, branched, cyclic or aromatic hydrocarbon radical, wherein G is selected from $C_1$-$C_{200000}$, preferably $C_1$-$C_{50000}$, most preferably $C_1$-$C_{2000}$, linear, branched, cyclic or aromatic hydrocarbon radicals, optionally substituted by one or more $C_1$-$C_{12}$ linear, branched, cyclic or aromatic groups (which radicals and/or which groups can be) optionally substituted by OH, COOH, COOR', F, Br, Cl, I, OR', $SO_3H$, $SO_3R'$ and SR' moieties; $ZPO_3M_2$; [V—N(K)]$_n$—K; [V—N(Y)]$_n$—V or [V—O]$_x$—V; wherein Y is $ZPO_3M_2$, [V—N(K)]$_n$—K or [V—N(K)]$_n$—V; and x is an integer from 1-50000; z is from 0-200000, whereby z is equal to or smaller than the number of carbon atoms in X, and a is 0 or 1; n is an integer from 0 to 50000; z=1 when a=0; and X is [V—N(K)]$_n$—K or [V—N(Y)]$_n$—V when z=0 and a=1;

Z is a $C_{1-6}$ alkylene chain;

M is H;

W is selected from H, X and $ZPO_3M_2$;

K is ZPO$_3$M$_2$ or H whereby K is ZPO$_3$M$_2$ when z=0 and a=1 or when W is H or X;
starting from tetra phosphorus hexa oxide comprising the steps of:
  adding P$_4$O$_6$ to an aqueous reaction medium containing a homogeneous Broensted acid, whereby the P$_4$O$_6$ will substantially quantitatively hydrolyse to phosphorous acid intermediate, said reaction medium being selected from:
i: an aqueous reaction medium containing an amine;
ii: an aqueous reaction medium wherein the amine is added simultaneously with the P$_4$O$_6$; and
iii: an aqueous reaction medium wherein the amine is added after the addition/hydrolysis of the P$_4$O$_6$ has been completed;
wherein the amine has the general formula:

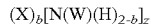

$(X)_b[N(W)(H)_{2-b}]_z$ wherein X is selected from C$_1$-C$_{200000}$, preferably C$_{1-50000}$, most preferably C$_{1-2000}$, linear, branched, cyclic or aromatic hydrocarbon radicals, optionally substituted by one or more C$_1$-C$_{12}$ linear, branched, cyclic or aromatic groups (which radicals and/or which groups can be) optionally substituted by OH, COOH, COOG, F, Br, Cl, I, OG, SO$_3$H, SO$_3$G and SG moieties; H; [V—N(H)]$_x$—H or [V—N(Y)]$_n$—V or [V—O]$_x$—V; wherein V is selected from: a C$_{2-50}$ linear, branched, cyclic or aromatic hydrocarbon radical, optionally substituted by one or more C$_{1-12}$ linear, branched, cyclic or aromatic groups (which radicals and/or groups are) optionally substituted by OH, COOH, COOR', F/Br/Cl/I, OR', SO$_3$H, SO$_3$R' or SR' moieties wherein R' is a C$_{1-12}$ linear, branched, cyclic or aromatic hydrocarbon radical; wherein G is selected from C$_1$-C$_{200000}$, preferably C$_1$-C$_{50000}$, most preferably C$_1$-C$_{20000}$, linear, branched, cyclic or aromatic hydrocarbon radicals, optionally substituted by one or more C$_1$-C$_{12}$ linear, branched, cyclic or aromatic groups (which radicals and/or which groups can be) optionally substituted by OH, COOH, COOR', F, Br, Cl, I, OR', SO$_3$H, SO$_3$R' and SR' moieties; H; [V—N(H)]$_n$—H; [V—N(Y)]$_n$—V or [V—O]$_x$—V; wherein Y is H, [V—N(H)]$_n$—H or [V—N(H)]$_n$—V and x is an integer from 1-50000; n is an integer from 0 to 50000; z is from 0-200000 whereby z is equal to or smaller than the number of carbon atoms in X, and b is 0 or 1; z=1 when b=0; and X is [V—N(H)]$_x$-H or [V—N(Y)]$_n$—V when z=0 and b=1;
W is selected from H and X;
whereby the free water level in the reaction medium, after the hydrolysis of the P$_4$O$_6$ has been completed, is in the range of from 0 to 40% by weight, expressed on the basis of the reaction medium before formaldehyde addition (100%), and wherein the addition of the homogeneous Broensted acid is effected so that, during the P$_4$O$_6$ hydrolysis, the pH of the reaction medium is at all times maintained below 5, followed by adding formaldehyde and a Broensted acid selected from homogeneous species having a pKa equal to or below 3.1 and/or specific heterogeneous species whereby the reactant ratios: (a) phosphorous acid, (b) amine, (c) formaldehyde and (d) Broensted acid are as follows:
(a):(b) of from 0.05:1 to 2:1;
(c):(b) of from 0.05:1 to 5:1;
(c):(a) of from 5:1 to 0.25:1; and
(b):(d) of from 40:1 to 1:5; (*)
(*) The ratio ((b):(d) in general) is based, for both species i.e. amine and catalyst and for both catalyst species i.e. homogeneous and heterogeneous, on the total amounts of the amine and the catalysts.

wherein (a) and (c) stand for the number of moles and (b) represents the number of moles multiplied by the number of N—H functions in the amine and (d) stands, for the homogeneous Broensted acid catalyst, for the number of moles of catalyst multiplied by the number of available protons per mole of catalyst and for the heterogeneous Broensted acid catalyst, (d) represents the number of catalyst proton equivalents; and
completing the reaction to thus yield the amino alkylene phosphonic acid.

In a preferred embodiment, the amino alkylene phosphonic acid is recovered.

Such amino alkylene phosphonic acids can, as an optional measure, subsequently be treated with alkali or earth alkali hydroxides or ammonia or amines to thus yield partial or total phosphonate salts. Suitable amines can be represented by the general formula $(X)_b[N(W)(H)_{2-b}]_z$ wherein the individual terms in said formula have the meaning as recited in claim 1, except that b can be 0, 1 or 2.

The preferred reactant ratios are as follows:
(a):(b) of from 0.1:1 to 1.50:1;
(c):(b) of from 0.2:1 to 2:1; and
(c):(a) of from 3:1 to 0.5:1.
Particularly preferred reactant ratios are:
(a):(b) of from 0.4:1 to 1.0:1.0;
(c):(b) of from 0.4:1 to 1.5:1; and
(c):(a) of from 2:1 to 1.0:1.
The preferred reactant ratios with respect to the Broensted acid are:
(b):(d) of from 20:1 to 1:3;
particularly preferred, in that respect, are:
(b):(d) of from 10:1 to 1:2.

The P$_4$O$_6$ is represented by a substantially pure compound containing at least 85%, preferably more than 90%; more preferably at least 95% and in one particular execution at least 97% of the P$_4$O$_6$. In a preferred embodiment the P$_4$O$_6$ used in the process of the invention comprises less than 1.0 weight % of elemental phosphorus. While tetraphosphorus hexa oxide, suitable for use within the context of this invention, can be manufactured by any known technology, in preferred executions the hexa oxide can be prepared in accordance with the process disclosed in EP 07 121 760.8 entitled "Process for the manufacture of P$_4$O$_6$". In detail, oxygen, or a mixture of oxygen and inert gas, and gaseous or liquid phosphorus are reacted in essentially stoichiometric amounts in a reaction unit at a temperature in the range from 1600 to 2000° K, by removing the heat created by the exothermic reaction of phosphorus and oxygen, while maintaining a preferred residence time of from 0.5 to 60 seconds, preferably at least 1 second, followed by quenching the reaction product, preferably to a temperature below 700° K. The hexa oxide so prepared is a pure product containing usually at least 97% of the oxide. The preferred residence time is from 5 to 30 seconds, more preferably from 8 to 30 seconds. The reaction product can, in one preferred execution, be quenched to a temperature below 350° K. In a further preferred embodiment the quenching is performed by adding liquid reaction product or liquid P$_4$O$_6$ as a coolant to the reaction product to be quenched.

The P$_4$O$_6$ (mp. 23.8° C.; bp. 173° C.) in liquid form is added to the aqueous reaction medium containing a homogeneous Broensted acid such that the pH of the reaction medium is at all times maintained below 5, said catalyst being homogeneously compatible with the reaction medium.

The P$_4$O$_6$ is added to the reaction mixture under stirring generally starting at ambient temperature. The reaction medium can contain the amine although the amine can also be added simultaneously with the P$_4$O$_6$ or after the addition (hydrolysis) of the $P_4O_6$ has been completed, whereby the pH of the reaction medium is maintained, at all times, below 5, preferably below 4, most preferably equal to or below 3.1.

The level of water present in the reaction mixture, after the hydrolysis of $P_4O_6$ has been completed, is in the range of from 0 to 40%, preferably 0 to 30%, calculated on the reaction mixture before the formaldehyde addition and the possibly additional Broensted acid for the subsequent reaction (100%). This reaction medium thus contains the $P_4O_6$ hydrolysate, the homogeneous Broensted acid and the amine, possibly as a salt. The water level shall be observed to favour and facilitate the reaction with the formaldehyde. The use of minimal levels of free water e.g. 0 to 20% constitutes one particularly preferred embodiment. The lower water levels were found to favour the yields of the amino alkylene phosphonic acids formed.

The hydrolysis is conducted at ambient temperature conditions (20° C.) up to about 150° C. While higher temperatures e.g. up to 200° C., or even higher, can be used such temperatures generally require the use of an autoclave or can be conducted in a continuous manner, possibly under autogeneous pressure built up. The temperature increase during the $P_4O_6$ addition can result from the exothermic hydrolysis reaction and was found to provide temperature conditions to the reaction mixture as can be required for the reaction with formaldehyde. The Broensted acid was found to favour the immediate, upon addition, hydrolysis of the $P_4O_6$ without undue accumulation of water insoluble $P_4O_6$ which is known to lead to unwanted dismutation products and also favours the reaction to proceed in the presence of stoichiometric levels of water or with low excess (vs. stoichiometric requirements) of water at high, well above ambient, temperature conditions. The homogeneous Broensted acid confers, during the $P_4O_6$ hydrolysis, to the reaction medium a pH (ambient temperature e.g. 25° C.) which shall at all times be below 5. In the event the $P_4O_6$ hydrolysis is conducted in the presence of the amine, i.e. the amine is present in the reaction medium before adding the $P_4O_6$ or the amine is added simultaneously with the $P_4O_6$, then the homogeneous Broensted acid shall preferably have a pKa equal to or below 3.1. When the amine is added to the reaction medium after the $P_4O_6$ hydrolysis has been completed, then any homogeneous Broensted acid can be used, even species having a pKa greater than 3.1, provided the pH of the reaction medium, controlled by the Broensted acid, is at all times below 5.

The subsequent, after the $P_4O_6$ hydrolysis has been completed, part of the reaction, specifically the reaction of the $P_4O_6$ hydrolysate, the amine and the formaldehyde, requires the presence of a Broensted acid catalyst selected from homogeneous species having a pKa equal to or below 3.1, preferably equal to or inferior to 2.75, most preferably equal to or inferior to 1.9, especially inferior to 1.9, and selected heterogeneous species. The Broensted acid is used in this part of the reaction in a ratio of amine (b) to (d) in the range of from 40:1 to 1:5 whereby (b) stands for the number of moles multiplied by the number of N—H functions in the amine; and (d) stands, in relation to the homogeneous Broensted acid, for the number of moles of acid catalyst multiplied by the number of available protons per mole of catalyst, and for the heterogeneous Broensted catalyst (d) represents the number of catalyst proton equivalents.

The pKa value for homogeneous Broensted catalyst is a well known variable which can be expressed as follows:

$$pKa = -\log_{10} Ka.$$

wherein Ka represents the thermodynamic equilibrium acidity constant.

The pKa values of practically all homogeneous Broensted acid substances are known from the literature or can, if this were needed, be determined conveniently. Homogeneous catalysts are catalysts adapted to form a single liquid phase within the reaction medium under the reaction conditions. It is understood that catalysts which are insoluble or immiscible in the reaction medium, and thus non-homogeneous, at ambient conditions e.g. 20° C., can become miscible or soluble at e.g. the reaction temperature and thus qualify as "homogeneous".

The homogeneous nature of an acid catalyst can be ascertained routinely by e.g. visible inspection of precipitation or phase separation properties.

The Broensted acid (catalyst) can also be represented by a heterogeneous Broensted acid. The Broensted property represents the capabilities of supplying protons. The term heterogeneous means that the acid catalyst is substantially insoluble in the reaction medium, at the reaction conditions, or substantially immiscible, thus liquid, in the reaction medium at the reaction conditions. The insoluble and/or immiscible nature of the catalyst can be ascertained routinely e.g. based on visible observation. Broensted acidity can also originate from Lewis acid properties after coordination of the Lewis site on the catalyst with a lone pair of electrons in a coordination partner e.g. water. The Broensted acidity can also be derived from the addition of a Lewis acid e.g. $BF_3$ to the Broensted acid catalyst precursor having a lone pair of electrons and being capable of coordinating with the Lewis acid e.g. silica.

The Broensted properties of any given acid catalyst are readily and routinely ascertainable. As an example, the Broensted acidity can be determined, for thermally stable inorganic products, by e.g. thermal desorption of isopropylamine followed by using a micro-balance in accordance with the method of R. J. Gorte et al., J. Catal. 129, 88, (1991) and 138, 714, (1992).

The amine component corresponds to the general formula:

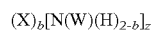

$$(X)_b[N(W)(H)_{2-b}]_z$$

wherein X is selected from $C_1$-$C_{200000}$, preferably $C_{1-50000}$, most preferably $C_{1-2000}$, linear, branched, cyclic or aromatic hydrocarbon radicals, optionally substituted by one or more $C_1$-$C_{12}$ linear, branched, cyclic or aromatic groups (which radicals and/or which groups can be) optionally substituted by OH, COOH, COOG, F, Br, Cl, I, OG, $SO_3H$, $SO_3G$ and SG moieties; H; [V—N(H)]$_x$—H or [V—N(Y)]$_n$—V or [V—O]$_x$—V; wherein V is selected from: a $C_{2-50}$ linear, branched, cyclic or aromatic hydrocarbon radical, optionally substituted by one or more $C_{1-12}$ linear, branched, cyclic or aromatic groups (which radicals and/or groups are) optionally substituted by OH, COOH, COOR', F/Br/Cl/I, OR', $SO_3H$, $SO_3R'$ or SR' moieties wherein R' is a $C_{1-12}$ linear, branched, cyclic or aromatic hydrocarbon radical; wherein G is selected from $C_1$-$C_{200000}$, preferably $C_1$-$C_{50000}$, most preferably $C_1$-$C_{2000}$, linear, branched, cyclic or aromatic hydrocarbon radicals, optionally substituted by one or more $C_1$-$C_{12}$ linear, branched, cyclic or aromatic groups (which radicals and/or which groups can be) optionally substituted by OH, COOH, COOR', F, Br, Cl, I, OR', $SO_3H$, $SO_3R'$ and SR' moieties; H; [V—N(H)]$_n$—H; [V—N(Y)]$_n$—V or [V—O]$_x$—V; wherein Y is H, [V—N(H)]$_n$—H or [V—N(H)]$_n$—V and x is an integer from 1-50000; n is an integer from 0 to 50000; z is from 0-200000 whereby z is equal to or smaller than the number of carbon atoms in X, and b is 0 or 1; z=1 when b=0; and X is [V—N(H)]$_x$—H or [V—N(Y)]$_n$—V when z=0 and b=1;

W is selected from H and X.

The essential amine component needed for synthesizing the inventive aminoalkylene phosphonic acids can be represented by a wide variety of known species. Examples of preferred amines include: imino di(acetic acid); ammonia; alkylene amines; alkoxy amines; halogen substituted alkyl amines; alkyl amines; and alkanol amines. It is understood that poly species are embraced. As an example, the term "alkyl amines" also includes—polyalkyl amines-, -alkyl polyamines- and -polyalkyl polyamines-.

Individual species of amines of interest include: ethylene diamine; diethylene triamine; triethylene tetraamine; tetraethylene pentamine; hexamethylene diamine; dihexamethylene triamine; 1,3-propane diamine-N,N'-bis(2-aminomethyl); polyether amines and polyether polyamines; 2-chloroethyl amine; 3-chloropropyl amine; 4-chlorobutyl amine; primary or secondary amines with $C_1$-$C_{25}$ linear or branched or cyclic hydrocarbon chains, in particular morpholine; n-butylamine; isopropyl amine; cyclohexyl amine; laurylamine; stearyl amine; and oleylamine; polyvinyl amines; polyethylene imine, branched or linear or mixtures thereof; ethanolamine; diethanolamine; propanolamine; and dipropanol amine.

In one embodiment of the inventive process the amine has the general formula:

$$(X)_a[N(W)(H)_{2-a}]_z$$

wherein X is selected from $C_1$-$C_{200000}$, preferably $C_{1-50000}$, most preferably $C_{1-2000}$, linear, branched, cyclic or aromatic hydrocarbon groups, optionally substituted by a $C_1$-$C_{12}$ linear, branched, cyclic or aromatic group (which chain and/or which group can be) optionally substituted by OH, COOH, COOR', F, Br, Cl, I, OR', $SO_3H$ and SR' moieties, wherein R' is a $C_1$-$C_{12}$ linear, branched, cyclic or aromatic hydrocarbon chain; H; $[A-N(W)]_x$-A or $[A-O]_x$-A wherein A is a $C_2$-$C_9$ linear, branched, cyclic or aromatic hydrocarbon chain and x is an integer from 1-50000, z is from 0-200000, and a is 0 or 1; z=1 when a=0; and X is $[A-N(W)]_x$-A when a=1 z=0;
W is selected from H, X, and $[V-N(H)]_n$-H, wherein V is selected from: a $C_{2-50}$ linear, branched, cyclic or aromatic hydrocarbon chain, optionally substituted by $C_{1-12}$ linear, branched, cyclic or aromatic groups (which chains and/or groups are) optionally substituted by OH, COOH, COOR', F/Br/Cl/I, OR', $SO_3H$ or SR' moieties wherein R' is a $C_{1-12}$ linear, branched, cyclic or aromatic hydrocarbon chain; and from $[A-O]_x$-A or $[A-N(W)]_x$-A, wherein A is a $C_{2-9}$ linear, branched, cyclic or aromatic hydrocarbon chain and x is an integer from 1-50000; and n is an integer from 0 to 50000;
thus leading to an aminoalkylene phosphonic acid having the general formula:

$$(X)_a[N(W)(ZPO_3M_2)_{2-a}]_z$$

wherein X is selected from $C_1$-$C_{200000}$, preferably $C_1$-$C_{50000}$, most preferably $C_1$-$C_{2000}$, linear, branched, cyclic or aromatic hydrocarbon chain, optionally substituted by a $C_1$-$C_{12}$ linear, branched, cyclic or aromatic group (which chain and/or which group can be) optionally substituted by OH, COOH, COOR', F, Br, Cl, I, OR', $SO_3H$ and SR' moieties, wherein R' is a $C_1$-$C_{12}$ linear, branched, cyclic or aromatic hydrocarbon chain; $ZPO_3M_2$; $[A-N(W)]_x$-A or $[A-O]_x$-A wherein A is a $C_2$-$C_9$ linear, branched, cyclic or aromatic hydrocarbon chain and x is an integer from 1-50000, z is from 0-200000, and a is 0 or 1; z=1 when a=0; and X is $[A-N(W)]_x$-A when z=0 and a=1;

Z is a $C_{1-6}$ alkylene chain;
M is selected from H and from alkali, earth alkali and ammonium ions and from protonated amines;
W is selected from H, X, $ZPO_3M_2$ and $[V-N(K)]_nK$, wherein V is selected from: a $C_{2-50}$ linear, branched, cyclic or aromatic hydrocarbon chain, optionally substituted by $C_{1-12}$ linear, branched, cyclic or aromatic groups (which chains and/or groups are) optionally substituted by OH, COOH, COOR', F/Br/Cl/I, OR', $SO_3H$ or SR' moieties wherein R' is a $C_{1-12}$ linear, branched, cyclic or aromatic hydrocarbon chain; and from $[A-O]_x$-A or $[A-N(W)]_x$-A, wherein A is a $C_{2-9}$ linear, branched, cyclic or aromatic hydrocarbon chain and x is an integer from 1-50000; and K is $ZPO_3M_2$ or H and n is an integer from 0 to 50000.

The essential formaldehyde component is a well known commodity ingredient. Formaldehyde sensu stricto known as oxymethylene having the formula $CH_2O$ is produced and sold as water solutions containing variable, frequently minor, e.g. 0.3-3%, amounts of methanol and are typically reported on a 37% formaldehyde basis although different concentrations can be used. Formaldehyde solutions exist as a mixture of oligomers. Such formaldehyde precursors can, for example, be represented by paraformaldehyde, a solid mixture of linear poly(oxymethylene glycols) of usually fairly short, n=8-100, chain length, and cyclic trimers and tetramers of formaldehyde designated by the terms trioxane and tetraoxane respectively.

The formaldehyde component can also be represented by aldehydes and ketones having the formula $R_1R_2C=O$ wherein $R_1$ and $R_2$ can be identical or different and are selected from the group of hydrogen and organic radicals. When $R_1$ is hydrogen, the material is an aldehyde. When both $R_1$ and $R_2$ are organic radicals, the material is a ketone. Species of useful aldehydes are, in addition to formaldehyde, acetaldehyde, caproaldehyde, nicotinealdehyde, crotonaldehyde, glutaraldehyde, p-tolualdehyde, benzaldehyde, naphthaldehyde and 3-aminobenzaldehyde. Suitable ketone species for use herein are acetone, methylethylketone, 2-pentanone, butyrone, acetophenone and 2-acetonyl cyclohexanone.

Examples of suitable species of the homogeneous Broensted acid for use herein can e.g. be represented by sulfuric acid, sulfurous acid, trifluoroacetic acid, trifluoromethane sulfonic acid, HCl, HBr, HI, methane sulfonic acid, oxalic acid, p-toluene sulfonic acid and naphthalene sulfonic acid. Mixtures of the acid catalyst species can also be used. Additional examples of homogeneous Broensted acid species can be represented by phosphorous acid, phosphoric acid and hypophosphorous acid.

Examples of the heterogeneous catalyst, having Broensted acid properties, can, by way of example, be represented by species of discretionary selected subclasses, namely:

(1) solid catalysts represented by acidic metal oxide combinations which can be supported onto usual carrier materials such as silica, carbon, silica-alumina combinations or alumina. These metal oxide combinations can be used as such or with inorganic or organic acid doping. Suitable examples of this class of catalysts are amorphous silica-alumina, acid clays, such as smectites, inorganic or organic acid treated clays, pillared clays, zeolites, usually in their protonic form, and metal oxides such as $ZrO_2$—$TiO_2$ in about 1:1 molar combination and sulfated metal oxides e.g. sulfated $ZrO_2$. Other suitable examples of metal oxide combinations, expressed in molar ratios, are: $TiO_2$—$SiO_2$ 1:1 ratio; and $ZrO_2$—$SiO_2$ 1:1 ratio.

(2) several types of cation exchange resins can be used as acid catalyst to carry out the reaction of an amine, phosphorous acid and a formaldehyde. Most commonly, such resins comprise copolymers of styrene, ethylvinyl benzene and divinyl benzene functionalized so as to graft $SO_3H$ groups onto the aromatic groups. Such resins are used as acidic catalysts in numerous commercial productions like e.g. in methyl t-butyl ether manufacturing from methanol and isobutene or in bisphenol A manufacturing starting from acetone and phenol. These acidic resins can be used in different physical configurations such as in gel form, in a macro-reticulated configuration or supported onto a carrier material such as silica or carbon or carbon nanotubes. Other types of resins include perfluorinated resins carrying carboxylic or sulfonic acid groups or both carboxylic and sulfonic acid groups. Known examples of such resins are: NAFION™, FLEMION™ and NEOSEPTA-F™. The fluorinated resins can be used as such or supported onto an inert material like silica or carbon or carbon nanotubes entrapped in a highly dispersed network of metal oxides and/or silica.

FLEMION is a Trademark of Asahi Glass, Japan
NEOSEPTA is a Trademark of Tokuyama Soda, Japan
NAFION is a trademark of DuPont, USA.

(3) a Broensted acid catalyst, such as an organic Broensted acid, which is substantially insoluble or immiscible in the reaction medium. The catalyst can form, at the reaction conditions, in particular the reaction temperature, a second liquid phase and can be recovered at the end of the reaction by conventional techniques such as filtration or phase separation. Examples of suitable acidic reagents include highly fluorinated, which means that 50% or more of the hydrogen atoms attached to the carbon atoms have been substituted by fluorine atoms, long chain sulfonic or carboxylic acids like perfluorinated undecanoic acid or more in particular perfluorinated carboxylic acid and perfluorinated sulfonic acids having from 6 to 24 carbon atoms. Such perfluorinated acid catalysts can be substantially immiscible in the reaction medium. The reaction will take place in a reactor under continuous stirring to ensure an adequate dispersion of the acid phase into the aqueous phase. The acidic reagent may itself be diluted into a water insoluble phase such as e.g. a water insoluble ionic liquid;

(4) heterogeneous solids, having usually a lone pair of electrons, like silica, silica-alumina combinations, alumina, zeolites, silica, activated charcoal, sand and/or silica gel can be used as support for a Broensted acid catalyst, like methane sulfonic acid or para-toluene sulfonic acid, or for a compound having a Lewis acid site, such as $SbF_5$, to thus interact and yield strong Broensted acidity. Heterogeneous solids, like zeolites, silica, or mesoporous silica e.g. MCM-41 or -48, or polymers like e.g. polysiloxanes can be functionalized by chemical grafting with a Broensted acid group or a precursor therefore to thus yield acidic groups like sulfonic and/or carboxylic acids and/or phosphonic acids or precursors therefore. The functionalization can be introduced in various ways known in the art like: direct grafting on the solid by e.g. reaction of the SiOH groups of the silica with chlorosulfonic acid; or can be attached to the solid by means of organic spacers which can be e.g. a perfluoro alkyl silane derivative. Broensted acid functionalized silica can also be prepared via a sol gel process, leading to e.g. a thiol functionalized silica, by co-condensation of $Si(OR)_4$ and e.g. 3-mercaptopropyl-tri-methoxy silane using either neutral or ionic templating methods with subsequent oxidation of the thiol to the corresponding sulfonic acid by e.g. $H_2O_2$. The functionalized solids can be used as is, i.e. in powder form, in the form of a zeolitic membrane, or in many other ways like in admixture with other polymers in membranes or in the form of solid extrudates or in a coating of e.g. a structural inorganic support e.g. monoliths of cordierite; and (5) heterogeneous heteropolyacids having most commonly the formula $H_xPM_yO_z$. In this formula, P stands for a central atom, typically silicon or phosphorus. Peripheral atoms surround the central atom generally in a symmetrical manner. The most common peripheral elements, M, are usually Mo or W although V, Nb, and Ta are also suitable for that purpose. The indices $_{x,y,z}$ quantify, in a known manner, the atomic proportions in the molecule and can be determined routinely. These polyacids are found, as is well known, in many crystal forms but the most common crystal form for the heterogeneous species is called the Keggin structure. Such heteropolyacids exhibit high thermal stability and are non-corrosive. The heterogeneous heteropolyacids are preferably used on supports selected from silica gel, kieselguhr, carbon, carbon nanotubes and ion-exchange resins. A preferred heterogeneous heteropolyacid herein can be represented by the formula $H_3PM_{12}O_{40}$ wherein M stands for W and/or Mo. Examples of preferred PM moieties can be represented by $PW_{12}$, $PMo_{12}$, $PW_{12}/SiO_2$, $PW_{12}/carbon$ and $SiW_{12}$.

While the homogeneous Broensted acid can be used during the $P_4O_6$ hydrolysis and during the subsequent amino alkylene phosphonic acid formation, this can, of course represent an advantage although such homogeneous catalysts can leave a residue within the final reaction product. Nevertheless, there are known techniques for recovering the acid catalyst from the reaction medium such as ion exchange, nano filtration or electrodialysis which can be used to solve or mitigate the problems. By contrast, the heterogeneous Broensted catalysts can easily be removed from the final reaction product by e.g. filtration of insoluble acids or phase separation of immiscible acids.

In a particularly preferred embodiment, the $P_4O_6$ hydrolysis is completed before adding the amine thus requiring reduced levels of the homogeneous Broensted acid. The reaction of the $P_4O_6$ hydrolysate, the amine and the formaldehyde is then conducted in the presence of a heterogeneous Broensted acid, which catalyst can easily be removed from the final product. In so proceeding, especially in conducting the reaction in using phosphorous acid as a Broensted acid catalyst for the $P_4O_6$ hydrolysis, the process can lead to a complete absence of chlorinated by-products as can result e.g. from using the traditional $PCl_3$ hydrolysis route. So proceeding can yield reaction products which can be used without cumbersome and expensive purification processes.

The reactant ratios, expressed as molar reactant ratios, are termed as follows:
(a)=phosphorous acid;
(b)=amine;
(c)=formaldehyde; and
(d)=Broensted acid
wherein (b) represents the number of moles (amine) multiplied by the number of N—H functions in the amine and (d) stands for the number of moles of homogeneous Broensted acid multiplied by the number of available protons per mole of catalyst or stands for the number of proton equivalents of the heterogeneous Broensted acid.

The Broensted acid catalyst can be homogeneous or heterogeneous with respect to the reaction medium and can be used as such or mixtures of homogeneous and heterogeneous species can also be used.

The heterogeneous catalyst herein is generally used in levels well known in the domain of the technology. The ultimate criteria for the determination of the catalyst level resides, of course, in the completeness of the reaction i.e. the conversion of $P_4O_6$ hydrolysate to phosphonic acid compounds. The quantitative heterogeneous catalyst level can thus, in that respect, be optimized routinely. Considering that the catalyst can be used throughout the entire reaction medium, e.g. a dispersed immiscible catalyst, or locally e.g. in a fixed bed or in a membrane or equivalent configurations, it is evident that in such cases the quantity of the catalyst cannot easily be defined in relation to the co-reactants. Irrespective of a correlation between the relative levels of the reactants, such as the amine and the catalyst, it was experimentally established that very low levels of the catalyst can yield, within the context of the inventive technology, beneficially high conversion to phosphonic acid. In particular, it was found that, in a batch process arrangement e.g. in a continuously stirred tank reactor (CSTR), the ratio of the amine (b) in direct (CSTR) contact with the heterogeneous catalyst (d) is generally in the range of from 40:1 to 1:5, (b) being expressed as the number of moles multiplied by the number of N—H functions in the amine. The catalyst (d) is expressed as the number of catalyst proton equivalents. In a fixed bed configuration only the amine (b) directly in contact with the heterogeneous catalyst (d) will be considered. In a fixed bed configuration the ratio of the amine (b) to the catalyst (d), expressed as indicated for the CSTR, is frequently in the range of from 10:1 to 1:40.

The reaction with formaldehyde is conducted in a manner routinely known in the domain of the technology. As illustrated in the experimental showings, the method can be conducted by combining the essential reactants and securing a reaction temperature by taking advantage of the exothermicity of the $P_4O_6$ hydrolysis and/or by heating in accordance with needs, usually within the range of from 45° C. to 200° C., and higher temperatures if elevated pressures are used, more preferably 70° C. to 150° C. The upper temperature limit actually aims at preventing any substantially undue thermal decomposition of the phosphorous acid reactant. It is understood and well known that the decomposition temperature of the phosphorous acid intermediate, and more in general of any other individual reactant, can vary depending upon additional physical parameters, such as pressure and the qualitative and quantitative parameters of the co-reactants in the reaction mixture.

The formaldehyde addition reaction can be conducted at ambient pressure and, depending upon the reaction temperature, under distillation of water, thereby also eliminating a minimal amount of non-reacted formaldehyde. The duration of the reaction can vary from virtually instantaneous, e.g. 1 minute, to an extended period of e.g. 4 hours. This duration generally includes the gradual addition, during the reaction, of formaldehyde. In one method set up, the phosphorous acid intermediate resulting from the $P_4O_6$ hydrolysis, the amine and the Broensted acid catalyst are added to the reactor in the specified sequence followed by heating this mixture under gradual addition of the formaldehyde component starting at a temperature e.g. in the range of from 45° C. to 200° C. This reaction can be carried out under ambient pressure with or without distillation of usually water and some non-reacted formaldehyde.

In another operational arrangement, the reaction can be conducted in a closed vessel under autogeneous pressure built up.

In yet another operational sequence, the reaction can be conducted in a combined distillation and pressure arrangement. Specifically, the $P_4O_6$ hydrolysis is conducted in a batch reactor under ambient pressure followed by circulating the $P_4O_6$ hydrolysate, the amine and the homogeneous Broensted acid catalyst through a reactor containing the heterogeneous Broensted acid catalyst under autogeneous pressure built up at a temperature from 45° C. to 200° C., under gradual addition of the formaldehyde, followed by returning the mixture to the batch reactor at ambient pressure and a temperature from 45° C. to 200° C. to thus eliminate part of the water and non-reacted ingredients. The heterogeneous Broensted acid catalyst can e.g. be represented by a sulfonic acid ion-exchange resin in a fixed bed mode or supported onto a suitable carrier material.

The foregoing process variables thus show that the reaction can be conducted by a variety of substantially complementary arrangements. The reaction can be conducted as a batch process by heating the reaction medium containing usually the $P_4O_6$ hydrolysate, the amine and the Broensted acid catalyst in a (1) closed vessel under autogeneous pressure built up, or (2) under reflux conditions, or (3) under distillation of water and minimal amounts of non-reacted formaldehyde, to a temperature preferably in the range of from 70° C. to 200° C. whereby the formaldehyde component is added, as illustrated in the Examples, gradually during the reaction. In a particularly preferred embodiment, the reaction is conducted in a closed vessel at a temperature in the range of from 100° C. to 200° C., coinciding particularly with the gradual addition of formaldehyde, within a time duration of from 1 minute to 60 minutes, in a more preferred execution from 1 minute to 20 minutes.

In another approach, the complete reaction sequence, namely the $P_4O_6$ hydrolysis and the subsequent reaction of the hydrolysate, the amine and the Broensted acid with the formaldehyde are conducted in a single continuous manner, possibly under autogeneous pressure, whereby the reaction temperature is preferably in the range of from 70° C. to 200° C. and the phosphonic acid reaction product is withdrawn on a continuous basis.

The method of manufacturing technology in accordance with this invention is illustrated by means of a series of examples as follows.

1. 4-Aminomethyl 1,8-octanediamine hex(methylene phosphonic acid)

To a solution of 28.95 g (0.167 mole) of 4-aminomethyl 1,8-octanediamine in 73.91 g (0.75 mole) of 37% aqueous hydrochloric acid are added drop wise 55 g (0.25 mole) of 98% pure tetraphosphorus hexaoxide in about 40 minutes under nitrogen and with stirring. During the tetraphosphorus hexaoxide addition, the temperature increased up to 82° C. At the end of the hydrolysis reaction, excess water amounts to 12.3% w/w of the total reaction mixture. The reaction mixture is further heated to 105° C. and 90.25 g (1.1 moles) of 36.6% aqueous solution of formaldehyde are added drop wise in 80 minutes under stirring with the reaction temperature comprised between 105 and 115° C. There after heating is continued for an additional period of 60 minutes at 105° C. $^{31}$P NMR analysis of the crude reaction mixture shows 96.1% of the 4-Aminomethyl 1,8-octanediamine hexa(methylene phosphonic acid); 1.2% of phosphorous acid; 0.8% of phosphoric acid and 1.9% of hydroxyl methyl phosphonic acid.

2. N-Phosphonomethyl imino diacetic acid

To a solution of 133. 1g (1 mole) of imino diacetic acid in 147.8 g (1.5 mole) of 37% aqueous hydrochloric acid are added drop wise 55 g (0.25 mole) of 98% pure tetraphosphorus hexaoxide in about 40 minutes under nitrogen and with stirring. During the tetraphosphorus hexaoxide addition, the temperature increased up to 77° C. At the end of the hydrolysis reaction, excess water amounts to about 20% w/w of the total reaction mixture which is a white slurry. The reaction mixture is further heated to 105° C. and 90.25 g (1.1 moles) of 36.6% aqueous solution of formaldehyde are added drop wise in 60 minutes under stirring with the reaction temperature comprised between 105 and 110° C. There after heating is continued for an additional period of 60 minutes at 105° C. The reaction mixture is a thick turbid solution which solidifies upon cooling. $^{31}$P NMR analysis of the crude reaction mixture shows 95.5% of the N-phosphonomethyl imino diacetic acid; 1.2% of phosphorous acid; 1.6% of phosphoric acid and 1.6% of hydroxyl methyl phosphonic acid.

3. Amino tri(methylene phosphonic acid)

To a solution of 17.63 g (0.33 mole) ammonium chloride in 35.4 g of water and 16.25 g (0.165 mole) of 37% aqueous hydrochloric acid are added drop wise 55 g (0.25 mole) of 98% pure tetraphosphorus hexaoxide in about 30 minutes under nitrogen and with stirring.

During the tetraphosphorus hexaoxide addition, the temperature increased up to 100° C. At the end of the hydrolysis reaction, excess water amounts to about 15% w/w of the total reaction mixture which is a clear liquid. The reaction mixture is further heated to 105° C. and 90.25 g (1.1 moles) of 36.6% aqueous solution of formaldehyde are added drop wise in 50 minutes under stirring with the reaction temperature comprised between 105 and 110° C. There after heating is continued for an additional period of 60 minutes at 105° C. $^{31}$P NMR analysis of the crude reaction mixture shows 82.2% of amino tri (methylene phosphonic acid); 11.6% of N-methyl imino bis (methylene phosphonic acid); 1.7% of phosphorous acid; 1.2% of phosphoric acid and 2.9% of hydroxyl methyl phosphonic acid.

4. Jeffamine D-230 tetra (methylene phosphonic acid) (*)

To a solution of 57.65 g (0.25 mole) Jeffamine D-230 in 27 g of water and 72.08 g (0.75 mole) of methane sulfonic acid are added drop wise 55 g (0.25 mole) of 98% pure tetraphosphorus hexaoxide in about 45 minutes under nitrogen and with stirring. During the tetraphosphorus hexaoxide addition, the temperature increased up to 68° C. At the end of the hydrolysis reaction, excess water amounts to 0% w/w of the total reaction mixture which is a clear liquid. The reaction mixture is further heated to 105° C. and 90.25 g (1.1 moles) of 36.6% aqueous solution of formaldehyde are added drop wise in 60 minutes under stirring with the reaction temperature comprised between 105 and 110° C. There after heating is continued for an additional period of 60 minutes at 105° C. $^{31}$P NMR analysis of the crude reaction mixture shows 95% of Jeffamine D-230 tetra (methylene phosphonic acid); 2.1% of phosphorous acid; 1.2% of phosphoric acid and 1.4% of hydroxyl methyl phosphonic acid.

(*) Jeffamine D-230 stands for: poly[oxy(methyl-1,2-ethanediyl)],α-(2-aminomethylethyl)-ω-(2-aminomethylethoxy)-—

5. Jeffamine T-403 hexa (methylene phosphonic acid) (**)

To a solution of 73.33 g (0.167 mole) Jeffamine T-403 in 73.91 g (0.75 mole) of 37% aqueous hydrochloric acid are added drop wise 55 g (0.25 mole) of 98% pure tetraphosphorus hexaoxide in about 45 minutes under nitrogen and with stirring. During the tetraphosphorus hexaoxide addition, the temperature increased up to 68° C. At the end of the hydrolysis reaction, excess water amounts to 9.7% w/w of the total reaction mixture which is a clear liquid. Reaction mixture is further heated to 105° C. and 90.25 g (1.1 moles) of 36.6% aqueous solution of formaldehyde are added drop wise in 60 minutes under stirring with the reaction temperature comprised between 105 and 110° C. There after heating is continued for an additional period of 60 minutes at 105° C. $^{31}$P NMR analysis of the crude reaction mixture shows 92.3% of Jeffamine T-403 hexa (methylene phosphonic acid); 5.3% of phosphorous acid; 0.6% of phosphoric acid and 1.8% of hydroxyl methyl phosphonic acid.

(**) Jeffamine T 403 stands for: poly[oxy(methyl-1,2-ethane diyl)], α-hydro-ω-(2-aminomethylethoxy)-, ether with 2-ethyl-2-(hydroxymethyl)-1,3-propanediol (3:1).

6. Amino tri(methylene phosphonic acid)

To a solution of 4.80 g (0.05 mole) methane sulfonic acid in 33.07 g of water are added drop wise 67.37 g (0.30 mole) of 98% pure tetraphosphorus hexaoxide in about 30 minutes under nitrogen and with stirring. During the tetraphosphorus hexaoxide addition, the temperature increased up to 100° C. Then after 125 g Amberlyst 15 wet resin and 27.2 g (0.4 moles) of 25% aqueous ammonia are added to the reaction mixture. Before formaldehyde addition excess water amounts to about 35.8% w/w of the total reaction mixture. Reaction mixture is further heated to 105° C. and 103.3 g (1.26 moles) of 36.6% aqueous solution of formaldehyde are added drop wise in 180 minutes under stirring with the reaction temperature comprised between 105 and 110° C. There after heating is continued for an additional period of 60 minutes at 105° C. $^{31}$P NMR analysis of the crude reaction mixture shows 71% of amino tri (methylene phosphonic acid); 7% of N-methyl imino bis (methylene phosphonic acid); 18% of phosphorous acid; 2% of phosphoric acid and 1.6% of hydroxyl methyl phosphonic acid.

7. n-Hexylamine bis(methylene phosphonic acid)

To a solution of 50.6 g (0.5 mole) n-hexylamine in 73.91 g (0.75 mole) of 37% aqueous hydrochloric acid are added drop wise 55 g (0.25 mole) of 98% pure tetraphosphorus hexaoxide in about 10 minutes under nitrogen and with stirring. During the tetraphosphorus hexaoxide addition temperature increased up to 83° C. At the end of the hydrolysis reaction, excess water amounts to 10.9% w/w of the total reaction mixture which is a clear liquid. Reaction mixture is further heated to 105° C. and 90.25 g (1.1 moles) of 36.6% aqueous solution of formaldehyde are added drop wise in 60 minutes under stirring with the reaction temperature comprised between 105 and 110° C. There after heating is continued for an additional period of 60 minutes at 105° C. $^{31}$P NMR analysis of the crude reaction mixture shows 96.1% of n-hexylamine bis (methylene phosphonic acid); 1% of phosphorous acid; 0.7% of phosphoric acid and 1.0% of hydroxyl methyl phosphonic acid.

8. 3-Chloropropylamino bis (methylene phosphonic acid)

To a solution of 65.01 g (0.5 mole) 3-chloropropyl amine hydrochloride in 73.91 g (0.75 mole) of 37% aqueous hydrochloric acid are added drop wise 55 g (0.25 mole) of 98% pure tetraphosphorus hexaoxide in about 30 minutes under nitrogen and with stirring. During the tetraphosphorus hexaoxide addition temperature increased up to 60° C. At the end of the hydrolysis reaction, excess water amounts to 10.1% w/w of the total reaction mixture which is a clear liquid. Reaction mixture is further heated to 105° C. and 90.25 g (1.1 moles) of 36.6% aqueous solution of formaldehyde are added drop wise in 70 minutes under stirring with the reaction temperature comprised between 105 and 110° C. There after heating is continued for an additional period of 60 minutes at 105° C. $^{31}$P NMR analysis of the crude reaction mixture shows 96.3% of 3-chloropropylamino bis (methylene phosphonic acid); 0.1% of phosphorous acid; 0.7% of phosphoric acid and 1.0% of hydroxyl methyl phosphonic acid.

9. N-Phosphonomethyl diethanolamine

To a solution of 105.14 g (1 mole) diethanolamine in 147.81 g (1.5 mole) of 37% aqueous hydrochloric acid are added drop wise 55 g (0.25 mole) of 98% pure tetraphosphorus hexaoxide in about 30 minutes under nitrogen and with stirring. During the tetraphosphorus hexaoxide addition temperature increased up to 65° C. At the end of the hydrolysis reaction, excess water amounts to 21% w/w of the total reaction mixture which is a clear liquid. Reaction mixture is further heated to 105° C. and 90.25 g (1.1 moles) of 36.6% aqueous solution of formaldehyde are added drop wise in 75 minutes under stirring with the reaction temperature comprised between 105 and 110° C. There after heating is continued for an additional period of 60 minutes at 105° C. $^{31}$P NMR analysis of the crude reaction mixture shows 47.3% of N-phosphonomethyl diethanolamine; 43.8% of the monocyclic ester derived from the N-phosphonomethyl diethanolamine; 1.3% of phosphoric acid and 0.7% of hydroxyl methyl phosphonic acid.

10. Diethylene triamine penta (methylene phosphonic acid)

To a solution of 20.64 g (0.2 mole) diethylene triamine in 88.69 g (0.9 mole) of 37% aqueous hydrochloric acid are added drop wise 55 g (0.25 mole) of 98% pure tetraphosphorus hexaoxide in about 30 minutes under nitrogen and with stirring. During the tetraphosphorus hexaoxide addition temperature increased up to 93° C. At the end of the hydrolysis reaction, excess water amounts to 17.5% w/w of the total reaction mixture which is a clear liquid. Reaction mixture is further heated to 105° C. and 90.25 g (1.1 moles) of 36.6% aqueous solution of formaldehyde are added drop wise in 75 minutes under stirring with the reaction temperature comprised between 105 and 110° C. There after heating is continued for an additional period of 60 minutes at 105° C. $^{31}$P NMR analysis of the crude reaction mixture shows 66.6% of diethylene triamine penta (methylene phosphonic acid); 24.3% of diethylene triamine tetra and tri (methylene phosphonic acid); 3.3% of phosphorous acid; 1.5% of phosphoric acid and 0.9% of hydroxyl methyl phosphonic acid.

The invention claimed is:

1. A method for the manufacture of aminoalkylene phosphonic acid having the general formula:

$$(X)_a[N(W)(Y)_{2-a}]_z$$

wherein X is selected from $C_1$-$C_{200000}$ linear, branched, cyclic or aromatic hydrocarbon radicals, optionally substituted by one or more $C_1$-$C_{12}$ linear, branched, cyclic or aromatic groups (which radicals and/or which groups can be) optionally substituted by OH, COOH, COOG, F, Br, Cl, I, OG, SO$_3$H, SO$_3$G and SG moieties; ZPO$_3$M$_2$; [V—N(IQ)$_n$]—K; [V—N(Y)]$_n$—V or [V—O]$_x$—V; wherein V is selected from: a $C_{2-50}$ linear, branched, cyclic or aromatic hydrocarbon radical, optionally substituted by one or more $C_{1-12}$ linear, branched, cyclic or aromatic groups (which radicals and/or groups are) optionally substituted by OH, COOH, COOR', F/Br/Cl/I, OR', SO$_3$H, SO$_3$R' or SR' moieties; wherein R' is a $C_{1-12}$ linear, branched, cyclic or aromatic hydrocarbon radical; wherein G is selected from $C_1$-$C_{200000}$ linear, branched, cyclic or aromatic hydrocarbon radicals, optionally substituted by one or more $C_1$-$C_{12}$ linear, branched, cyclic or aromatic groups (which radicals and/or which groups can be) optionally substituted by OH, COOH, COOR', F, Br, Cl, I, OR', SO$_3$H, SO$_3$R' and SR' moieties; ZPO$_3$M$_2$; [V—N(IQ)$_n$]—K; [V—N(Y)]$_n$—V or [V—O]$_x$—V; wherein Y is ZPO$_3$M$_2$, [V—N(K)]$_n$—K or [V—N(K)]$_n$—V; and x is an integer from 1-50000; z is from 0-200000, whereby z is equal to or smaller than the number of carbon atoms in X, and a is 0 or 1; n is an integer from 0 to 50000; z=1 when a=0; and X is [V—N(K)]$_n$—K or [V—N(Y)]$_n$—V when z=0 and a=1;

Z is a $C_{1-6}$ alkylene chain;

M is H;

W is selected from H, X and ZPO$_3$M$_2$;

K is ZPO$_3$M$_2$ or H whereby K is ZPO$_3$M$_2$ when z=0 and a=1 or when W is H or X; starting from tetra phosphorus hexa oxide comprising the steps of:

adding P$_4$O$_6$ to an aqueous reaction medium containing a homogeneous Broensted acid and an amine whereby the P$_4$O$_6$ will substantially quantatively hydrolyse to phosphorous acid intermediate, or adding P$_4$O$_6$ and an amine simultaneously to an aqueous reaction medium containing a homogeneous Broensted acid, whereby the P$_4$O$_6$ will substantially quantatively hydrolyze to phosphorous acid intermediate; or adding P$_4$O$_6$ to an aqueous reaction medium containing a homogeneous Broensted acid, whereby the P$_4$O$_6$ will substantially quantatively hydrolyse to phosphorous acid intermediate, wherein an amine is added after the addition/hydrolysis of the P$_4$O$_6$ has been completed;

wherein the amine has the general formula:

$$(X)_b[N(W)(H)_{2-b}]_z$$

wherein X is selected from $C_1$-$C_{200000}$ linear, branched, cyclic or aromatic hydrocarbon radicals, optionally substituted by one or more $C_1$-$C_{12}$ linear, branched, cyclic or aromatic groups (which radicals and/or which groups can be) optionally substituted by OH, COOH, COOG, F, Br, Cl, I, OG, SO$_3$H, SO$_3$G and SG moieties; H; [V—N(H)J$_x$]—H or [V—N(Y)J$_n$]—V or [V—O]$_x$—V; wherein V is selected from: a $C_{2-50}$ linear, branched, cyclic or aromatic hydrocarbon radical, optionally substituted by one or more $C_{1-12}$ linear, branched, cyclic or aromatic groups (which radicals and/or groups are) optionally substituted by OH, COOH, COOR', F/Br/Cl/I, OR', SO$_3$H, SO$_3$R' or SR' moieties; wherein R' is a $C_{1-12}$ linear, branched, cyclic or aromatic hydrocarbon radical; wherein G is selected from $C_1$-$C_{200000}$, linear, branched, cyclic or aromatic hydrocarbon radicals, optionally substituted by one or more $C_1$-$C_{12}$ linear, branched, cyclic or aromatic groups (which radicals and/or which groups can be) optionally substituted by OH, COOH, COOR', F, Br, Cl, I, OR', SO$_3$H, SO$_3$R' and SR' moieties; H; [V—N(H)]$_n$—H; [V—N(Y)J$_n$—V or [V—O]$_x$—V; wherein Y is H, [V—N(H)]$_n$—H or [V—N(H)]$_n$—V and x is an integer from 1-50000, n is an integer from 0 to 50000; z is from 0-200000 whereby z is equal to or smaller than the number of carbon atoms in X, and b is 0 or 1; z=1 when b=0; and X is [V—N(H)J$_x$—H or [V—N(Y)J$_n$—V when z=0 and b=1;

W is selected from H and X;

whereby the free water level in the reaction medium, after the hydrolysis of the $P_4O_6$ has been completed, is in the range of from 0 to 40% by weight and wherein the addition of the homogeneous Broensted acid is effected so that, during the $P_4O_6$ hydrolysis, the pH of the reaction medium is at all times maintained below 5, followed by adding formaldehyde and a Broensted acid selected from homogeneous species having a pKa equal to or below 3.1 and specific heterogeneous species whereby the reactant ratios: (a) phosphorous acid, (b) amine, (c) formaldehyde and (d) Broensted acid are as follows:

(a):(b) of from 0.05:1 to 2:1;
(c):(b) of from 0.05:1 to 5:1;
(c):(a) of from 5:1 to 0.25:1; and
(b):(d) of from 40:1 to 1:5;

wherein (a) and (c) stand for the number of moles and (b) represents the number of moles multiplied by the number of N—H functions in the amine and (d) stands, for the homogeneous Broensted acid, for the number of moles of catalyst multiplied by the number of available protons per mole of catalyst; and for the heterogeneous Broensted acid, for the number of catalyst proton equivalents; and completing the reaction to thus yield the amino alkylene phosphonic acid, wherein the heterogeneous Broensted acid catalyst is selected from the group of:
(1) solid acidic metal oxide combinations as such or supported onto a carrier material;
(2) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;
(3) organic sulfonic and carboxylic and phosphonic Broensted acids which are substantially immiscible in the reaction medium at the reaction temperature;
(4) an acid catalyst derived from:
  (i) the interaction of a solid support having a lone pair of electrons onto which is deposited an organic Broensted acid; or
  (ii) the interaction of a solid support having a lone pair of electrons onto which is deposited a compound having a Lewis acid site;
  (iii) heterogeneous solids functionalized by chemical grafting with a Broensted acid group or a precursor therefore, and
(5) heterogeneous heteropolyacids of the general formula $H_xPM_yO_z$ wherein P is selected from phosphorus and silicon and M is selected from W and Mo and combinations thereof.

2. The method in accordance with claim 1 whereby, during the hydrolysis of the $P_4O_6$, the pH of the reaction medium is maintained below 4 and the free water level is in the range of from 0 to 30% by weight.

3. The method in accordance with claim 1 wherein the homogeneous Broensted acid has a pKa equal to or below 2.75 and is selected from the group of sulfuric acid, sulfurous acid, trifluoroacetic acid, trifluoromethane sulfonic acid, HCl, HBr, HI, methane sulfonic acid, oxalic acid, malonic acid, p-toluene sulfonic acid and naphthalene sulfonic acid, phosphorous acid, phosphoric acid and hypophosphorous acid and mixtures thereof.

4. The method in accordance with claim 1 wherein the heterogeneous Broensted acid added with the formaldehyde is a heterogeneous Broensted acid.

5. The method in accordance with claim 1 wherein the amine is selected from: ammonia; alkylene amines; alkoxy amines; halogen substituted alkyl amines; alkyl amines; and alkanol amines.

6. The method in accordance with claim 1 wherein the $P_4O_6$ used is prepared by reacting gaseous or liquid phosphorus with oxygen, or a mixture of oxygen and an inert gas, in essentially stoichiometric amounts, in a reactor at an average temperature in the range from 1600 K to 2000 K, by removing the heat created by the exothermic reaction of phosphorus and oxygen, with a residence time from 0.5 to 60 seconds followed by quenching the reaction product to a temperature below about 700 K.

7. The method in accordance with claim 6 wherein the reaction product is quenched to a temperature below about 350 K and wherein the residence time is from 8 to 30 seconds.

8. The method in accordance with claim 1 wherein the amine is added to the reaction medium after the $P_4O_6$ hydrolysis has been completed.

9. The method in accordance with claim 1 wherein the reactant ratios are:
(a):(b) of from 0.1:1 to 1.50:1;
(c):(b) of from 0.2:1 to 2:1;
(c):(a) of from 3:1 to 0.5:1; and
(b):(d) of from 20:1 to 1:3.

10. The method in accordance with claim 1 comprising reacting the $P_4O_6$ hydrolysate, the amine and the Broensted acid catalyst, at a temperature in the range from 45° C. to 200° C., under gradual addition of formaldehyde, in an arrangement selected from:
a closed vessel under autogeneous pressure built up;
an open vessel under reflux conditions; or
under distillation of water and minimal amounts of non-reacted formaldehyde.

11. The method in accordance with claim 10 wherein the reaction is conducted in a closed vessel at a temperature in the range from 100° C. to 200° C. for a period of from 1 to 60 minutes.

12. The method in accordance with claim 1 wherein the $P_4O_6$ hydrolysis and the reaction of the $P_4O_6$ hydrolysate, the amine and the Broensted acid catalyst with the formaldehyde is conducted in a single continuous manner, possibly under autogeneous pressure built up, at a temperature from 45° C. to 200° C. and the phosphonic acid reaction product is withdrawn on a continuous basis.

13. The method in accordance with claim 1 wherein the $P_4O_6$ hydrolysis is conducted in a batch reactor under ambient pressure followed by circulating the $P_4O_6$ hydrolysate, the amine and the homogeneous Broensted acid catalyst through a reactor containing the heterogeneous Broensted acid catalyst under autogeneous pressure built up at a temperature from 45° C. to 200° C., under gradual addition of the formaldehyde, followed by returning the mixture to the batch reactor at ambient pressure and a temperature from 70° C. to 200° C. to thus eliminate part of the water and non-reacted ingredients.

14. The method in accordance with claim 1 wherein the reactant ratios are:
(a):(b) of from 0.4:1 to 1.0:1.0;
(c):(b) of from 0.4:1 to 1.5:1;
(c):(a) of from 2:1 to 1.0:1; and
(b):(d) of from 10:1 to 1:2.

15. The method in accordance with claim 1 wherein the aminoalkylene phosphononic acid has the formula: (X)N(W)(ZPO$_3$M$_2$)

wherein X and W are independently selected from: $CH_2COOH$; $CH_2COOR$; and $CH_2CH_2OH$; Z is $CH_2$; and R is selected from $C_1$-$C_{12}$.

16. The method in accordance with claim 15 wherein $X=W=CH_2COOH$.

* * * * *